US007578976B1

(12) United States Patent
Northrup et al.

(10) Patent No.: US 7,578,976 B1
(45) Date of Patent: Aug. 25, 2009

(54) SLEEVE REACTION CHAMBER SYSTEM

(75) Inventors: M. Allen Northrup, Berkeley, CA (US); Barton V. Beeman, San Mateo, CA (US); William J. Benett, Livermore, CA (US); Dean R. Hadley, Manteca, CA (US); Phoebe Landre, Livermore, CA (US); Stacy L. Lehew, Livermore, CA (US); Peter A. Krulevitch, Pleasanton, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 792 days.

(21) Appl. No.: 09/568,618

(22) Filed: May 10, 2000

(51) Int. Cl.
*G01N 33/00* (2006.01)

(52) U.S. Cl. ........................ 422/102; 422/109; 422/138

(58) Field of Classification Search ................. 422/102, 422/109, 138
See application file for complete search history.

(56) References Cited

U.S. PATENT DOCUMENTS 4,314,008 A * 2/1982 Blake ............................ 429/8
4,865,986 A * 9/1989 Coy et al. ................ 435/285.1
5,415,841 A * 5/1995 Dovichi et al. ............. 422/68.1
5,641,400 A * 6/1997 Kaltenbach et al. ...... 210/198.2

* cited by examiner

*Primary Examiner*—Sam P Siefke
(74) *Attorney, Agent, or Firm*—James S. Tak; Alan H. Thompson; John H. Lee

(57) ABSTRACT

A chemical reaction chamber system that combines devices such as doped polysilicon for heating, bulk silicon for convective cooling, and thermoelectric (TE) coolers to augment the heating and cooling rates of the reaction chamber or chambers. In addition the system includes non-silicon-based reaction chambers such as any high thermal conductivity material used in combination with a thermoelectric cooling mechanism (i.e., Peltier device). The heat contained in the thermally conductive part of the system can be used/reused to heat the device, thereby conserving energy and expediting the heating/cooling rates. The system combines a micromachined silicon reaction chamber, for example, with an additional module/device for augmented heating/cooling using the Peltier effect. This additional module is particularly useful in extreme environments (very hot or extremely cold) where augmented heating/cooling would be useful to speed up the thermal cycling rates. The chemical reaction chamber system has various applications for synthesis or processing of organic, inorganic, or biochemical reactions, including the polymerase chain reaction (PCR) and/or other DNA reactions, such as the ligase chain reaction.

13 Claims, 2 Drawing Sheets

SLEEVE REACTION CHAMBER SYSTEM

The United States Government has rights in this invention pursuant to Contract No. W-7405-ENG48 between the United States Department of Energy and the University of California for the operation of Lawrence Livermore National Laboratory.

BACKGROUND OF THE INVENTION

The present invention relates to chemical reaction chambers, particularly to a chemical reaction chamber combined with means for augmenting heat/cooling using the Peltier effect, and more particularly to a micromachined silicon or high thermal conductivity reaction chamber in combination with devices such as doped polysilicon for heating, bulk silicon for convective cooling, and thermoelectric coolers to augment the heating and cooling rates of such chambers.

Instruments generally used for performing chemical synthesis through thermal control and cycling are very large (table-top size) and inefficient. They typically work by heating and cooling a large thermal mass (e.g. an aluminum block) that has inserts for test tubes. Recently, efforts have been directed to miniaturize these instruments by designing and constructing reaction chambers out of silicon and silicon-based materials (e.g., silicon nitride, polycrystalline silicon) that have integrated heaters and cooling via convection through the silicon. Those miniaturization efforts are exemplified by copending U.S. application Ser. No. 07/938,106, filed Aug. 31, 1992, entitled "Microfabricated Reactor now U.S. Pat. No. 5,639,423 issued Jun., 17, 1997"; Ser. No. 08/489,819, filed Jun. 13, 1995, entitled "Diode Laser Heated Micro-Reaction Chamber with Sample Detection Means"; and Ser. No. 08/492,678 filed Jun. 20, 1995, entitled "Silicon-Based Sleeve Devices for Chemical Reactions now U.S. Pat. No. 5,589,136 issued Dec. 31, 1996," each assigned to the same assignee.

The present invention is a chemical reaction chamber that combines doped polysilicon for heating, bulk silicon for convective cooling, and thermoelectric devices to augment the heating and cooling rates of the chamber. The combination of the reaction chamber with the thermoelectric device enables the heat contained in the thermally conductive areas to be used/reused to heat the device, thereby conserving energy and expediting the heating/cooling rates. The chemical reaction chamber may be composed of micromachined silicon or any high thermal conductivity material. The thermoelectric mechanism comprises, for example, a Peltier device.

SUMMARY OF THE INVENTION

An object of the present invention is to provide reaction chambers for thermal cycling.

A further object of the invention is to provide a Peltier-assisted microfabricated reaction chamber for thermal cycling.

A further object of the invention is to combine a microfabricated reaction chamber with an additional device for augmented heating/cooling using the Peltier effect.

Another object of the invention is to provide a chemical reaction chamber constructed of silicon-based or non-silicon-based materials in combination with a thermoelectric cooling mechanism.

Another object of the invention is to combine a microfabricated chemical reaction chamber with a Peltier type heating/cooling mechanism.

Another object of the invention is to combine a sleeve-type micromachined silicon reaction chamber with a Peltier effect device for augmented heating/cooling, which enables use of the reaction chamber in extreme high or low temperature environments.

Other objects and advantages of the present invention will become apparent from the following description and accompanying drawing. The invention involves a silicon-based or non-silicon-based microfabricated reactor with a thermoelectric (i.e. Peltier effect) cooler/heater to augment the thermal cycling rates. The reaction chamber may be constructed of silicon or silicon-based materials (e.g., silicon nitride, polycrystalline silicon) or non-silicon-based, high thermal conductivity materials (e.g., copper, aluminum, etc.). The Peltier effect thermoelectric heater/coolers (heat pumps) are used to rapidly cycle the temperature of the micro reaction chamber. The reaction chamber system may be constructed to include an array of individual chambers located in a sleeve-type silicon-based reaction chamber arrangement. The illustrated embodiment has been experimentally utilized as a thermal cycling instrumentation for the polymerase chain reaction and other chemical reactions. By these experiments the invention has been shown to be superior to present commercial instruments on thermally-driven chemical reactions.

BRIEF DESCRIPTION OF THE DRAWINGS

The accompanying drawing, which is incorporated into and forms a part of the disclosure, illustrates an embodiment of the invention and, together with the description, serves to explain the principles of the invention.

DETAILED DESCRIPTION OF THE INVENTION

Figure 1:
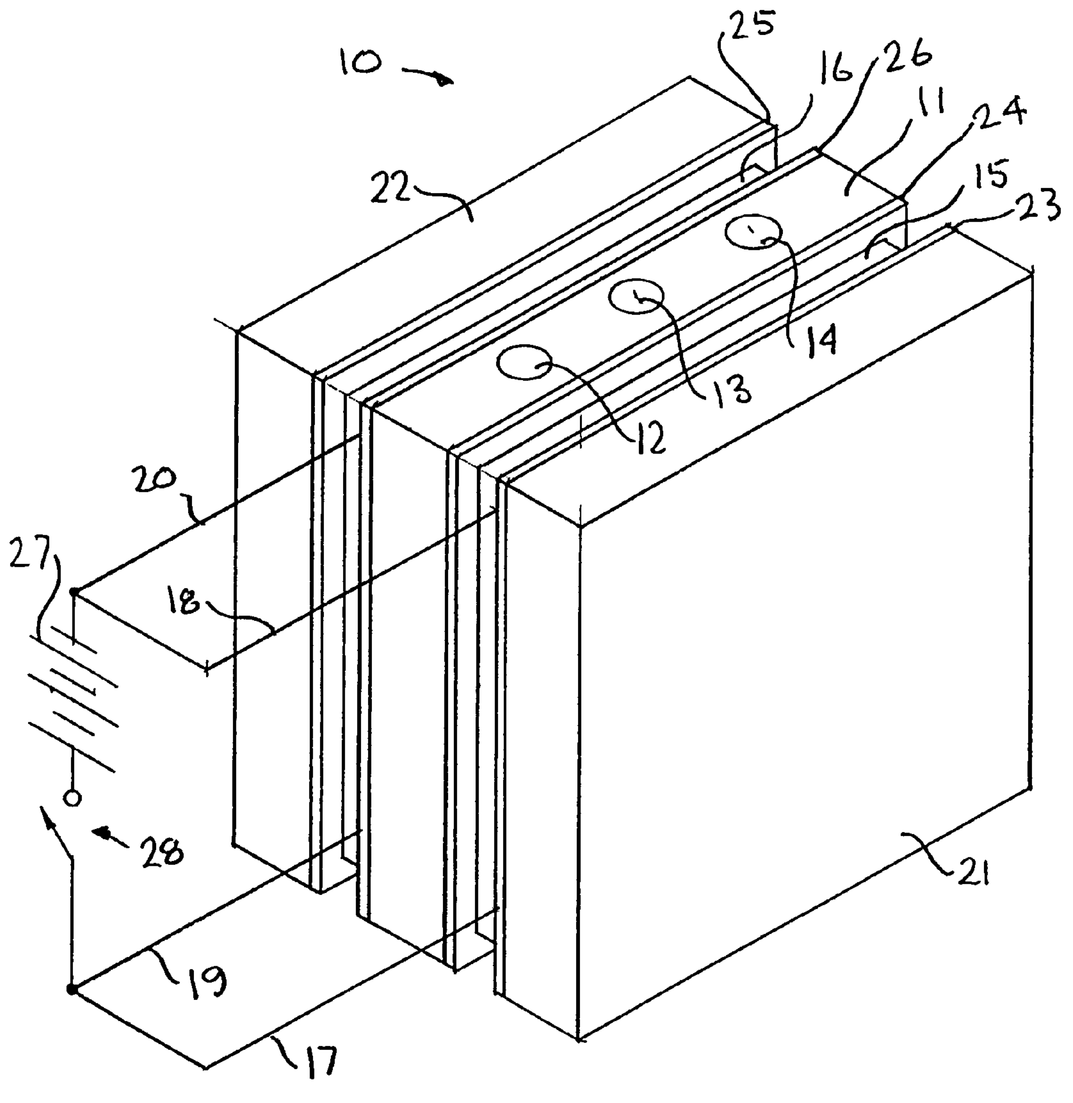
FIG. 1 is a perspective view of an embodiment of a Peltier-assisted microfabricated reaction chamber system made in accordance with the present invention.

The present invention involves Peltier-assisted microfabricated reaction chambers for thermal cycling. The microfabricated reactor may be constructed of silicon or silicon-based materials, such as silicon nitride and polycrystalline silicon, or of non-silicon-based, high thermal conductivity materials, such as copper, aluminum, etc., used in combination with a thermoelectric (TE) cooling mechanism, such as a Peltier device. The disclosed embodiment involves silicon-based sleeve-type reaction chambers with a specific arrangement of the TE device such that the TE device functions as a TE heater/cooler wherein the heat contained in the thermally conductive portion thereof can be used/reused to heat the reaction chambers, thereby conserving energy and expediting the heating/cooling rates. The disclosed embodiment of the invention combines a micromachined silicon reaction chamber with an additional module (TE heater/cooler) for augmented heating/cooling using the Peltier effect. This additional module is particularly useful in extreme temperature environments where augmented heating/cooling would speed up the thermal cycling rates.

The silicon-based micro-reactor chambers may be constructed as described in above-referenced copending application Ser. No. 08/492,678 and the fabrication process thereof is incorporated herein.

The Peltier effect has been well understood for many years and in recent years Peltier heat pumps have become commercially available. This invention uses off-the-shelf Peltier coolers (heat pumps) to rapidly cycle the temperature of the silicon-based micro chamber array.

Peltier heat pumps are semiconductor devices typically with two planner surfaces. When a direct current (dc) source is applied to the heat pump, heat is moved from one surface to the other. If the polarity is reversed the heat is pumped in the opposite direction.

The rapid thermal cycling is accomplished by shuttling the heat from a thermal reservoir, such as a copper block, to the reaction chamber(s) and then back to the thermal reservoir using one or more Peltier heat pumps. The cycle starts by pumping the heat from the reservoir into the test device (reaction chamber) to heat it to the desired temperature. Using the heat from the reservoir to heat the device lowers the temperature of the reservoir thereby increasing the $\Delta T$ between the chamber and the reservoir. When the polarity of the heat pump is reversed the heat is pumped from the device back to the reservoir. Because the $\Delta T$ between the device and the reservoir has been increased the thermal transfer occurs much faster.

The active thermal system can be insulated from the ambient temperature and no external source of heat is required. The system can be speeded up by thermally biasing the temperature of the entire thermal system to be near the center of the range of the temperature cycle. In the case of a planner type device such as a micro PCR chamber array illustrated in the drawing, good temperature uniformly can be accomplished by applying heat pumps and thermal reservoirs to both planner surfaces of the test device (chamber array). A more cube-like configured test device might require heat pumps on four or five surfaces to achieve rapid cycling and good uniformity.

FIG. 1 illustrates an embodiment of the system of the invention using a planner type test device or reaction chamber array with a Peltier type device and a thermal reservoir positioned on opposite sides of the reaction chamber array. The system generally indicated at 10 comprises a test device 11 which includes three reaction chambers 12,13, and 14 into which material to be tested is inserted as known in the art. By way of example the device 11 may have a length of 1.0 cm, width of 1.0 cm, and thickness of 2 mm. Peltier heat pumps 15 and 16 are positioned adjacent opposite sides of the test device 11 with electrical leads or contacts 17-18 and 19-20, respectively, extending therefrom. By way of example heat pumps 15 and 16 may be constructed of bismuth tellurium with a thickness of 2 mm. Thermal reservoirs 21 and 22 are positioned adjacent the Peltier heat pumps. The Peltier heat pumps 15 and 16 are secured to test device 11 and to thermal reservoirs 21 and 22 by bonding, pressure fit, or clamping, indicated at 23-24 and 25-26, or other means using material which is highly thermally conductive, such as thermal epoxy, so as to minimize heat loss during transfer from the reservoirs to or from the test device. By way of example thermal reservoirs may be constructed of copper, aluminum, silicon, or other highly thermal conductive materials such as aluminum-based ceramics or cermets with a thickness of 5 mm.

Figure 2:
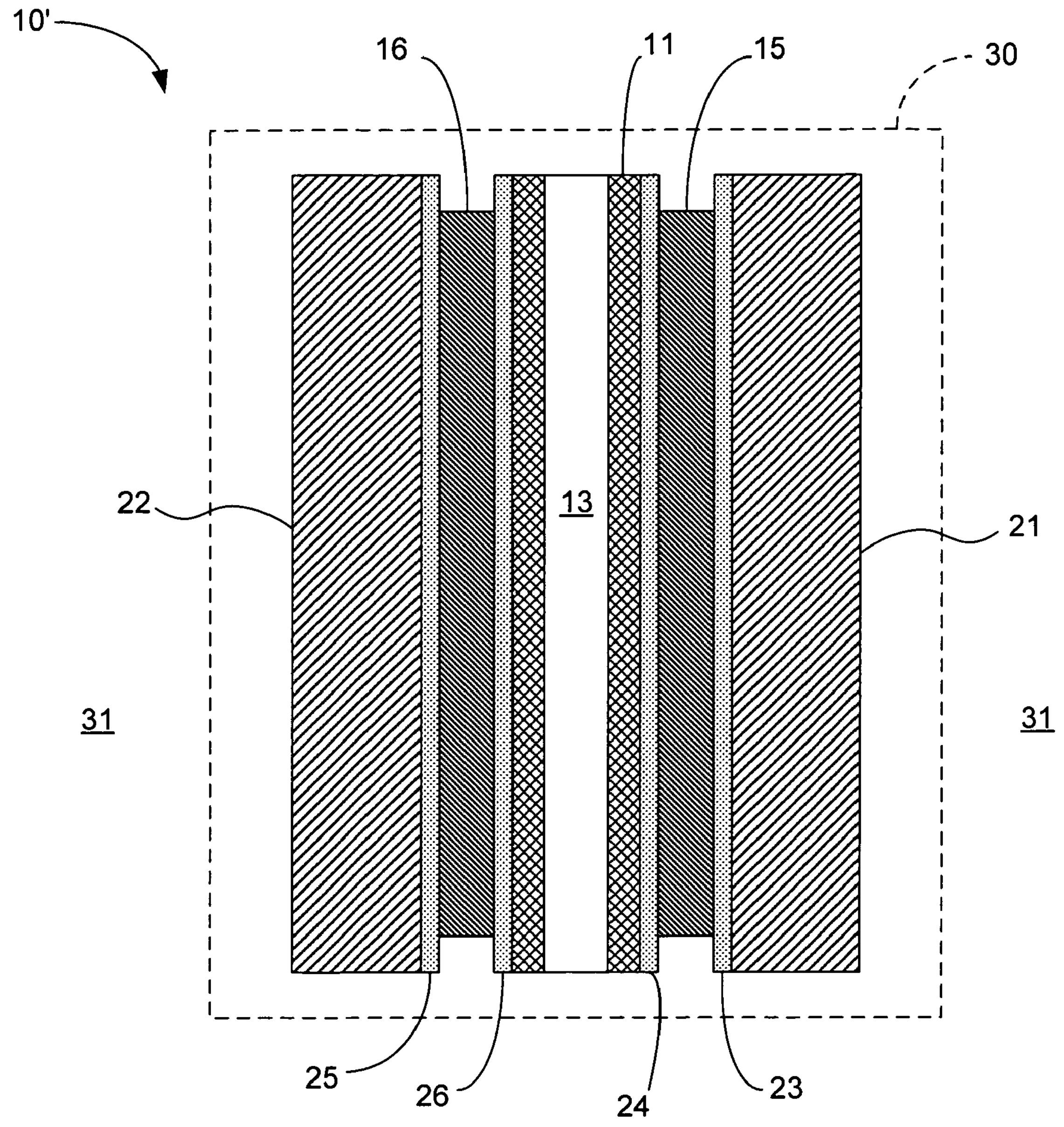
FIG. 2 is a cross-sectional view of the system shown in FIG. 1 taken through the reaction chamber 13, and additionally shown with insulation 30.

And FIG. 2 shows a cross-sectional view of a second embodiment of the system indicated at 10' which is essentially the same system 10 shown in FIG. 1 with the exception of insulation 30 which surrounds the active thermal system. The insulation 30 operates to insulate the system from the ambient temperature of the surrounding space indicated at 31.

The electrical leads or contacts 17-20 are connected to an appropriate power supply and switching arrangement schematically illustrated at 27 and 28.

It has thus been shown that the present invention provides a system including a reaction chamber having augmented heating/cooling capabilities whereby the system can be utilized in extreme (hot and cold) temperature environments, and the Peltier effect heating/cooling arrangement provides rapid thermal cycling. The system can be used for synthesis or processing or organic, inorganic, or biochemical reactions. The additional power required for the TE heater/cooler is not prohibitive, particularly for operation in more extreme environments.

While a particular embodiment of the invention has been illustrated and described, such is not intended to be limiting. Modifications and changes may become apparent to those skilled in the art, and it is intended that the invention be limited only by the scope of the appended claims.

The invention claimed is:

1. An improved sleeve reaction chamber system, the improvement comprising:

at least one Peltier heat pump located adjacent a sleeve reaction chamber device, a thermal reservoir located adjacent said at least one Peltier heat pump opposite said sleeve reaction chamber device and insulated from the ambient temperature, and means for reversibly activating said Peltier heat pump to store heat in the thermal reservoir pumped from the sleeve reaction chamber device during a cooling stage and reuse the stored heat from the thermal reservoir to heat the sleeve reaction chamber device during a heating stage.

2. The improved system of claim 1, wherein said sleeve reaction chamber device includes a plurality of reaction chambers.

3. The improved system of claim 1, wherein a Peltier heat pump and a thermal reservoir are located on a plurality of sides of said sleeve reaction chamber device.

4. The improved system of claim 1, wherein a Peltier heat pump and a thermal reservoir are located on each of two opposite sides of said sleeve reaction chamber device.

5. The improved system of claim 1, wherein said sleeve reaction chamber device is constructed of materials selected from the group consisting of silicon-based and non-silicon based materials.

6. The improved system of claim 5, wherein said sleeve reaction chamber is constructed of silicon-based materials selected from the group of silicon, silicon nitride, and polycrystalline silicon.

7. The improved system of claim 5, wherein said sleeve reaction chamber is constructed of a thermal conductivity metal.

8. The improved system of claim 1, wherein said thermal reservoir is constructed of material selected from the group consisting of copper, aluminum, silicon, and aluminum-based ceramics.

9. The improved system of claim 1, wherein said thermal reservoir is secured to said Peltier heat pump by bonding, pressure fit, or clamping; and wherein said Peltier heat pump is secured to said sleeve reaction chamber device by bonding, clamping, or pressure fit.

10. In a microfabricated silicon-based reaction chamber device, the improvement comprising:

energy conserving means for thermal cycling heat to and from said reaction chamber device by pumping heat from said reaction chamber to at least one thermal reservoir insulated from the ambient temperature for storage therein to cool said reaction chamber device, and reusing the stored heat from said thermal reservoir to heat said reaction chamber device, said means including at least one Peltier effect heating/cooling device comprising a Peltier heat pump and an adjacent thermal reservoir.

11. The improvement of claim 10, wherein said thermal reservoir is secured to said Peltier heat pump and said Peltier heat pump is secured to said reaction chamber device.

12. The improvement of claim 10, wherein said reaction chamber device comprises a sleeve reaction device having at least one reaction chamber therein.

13. The improvement of claim 10, wherein a Peltier heat pump and a thermal reservoir are positioned on each of two opposite sides of said sleeve reaction device.

* * * * *